United States Patent [19]

Vuyts et al.

[11] 4,148,659

[45] Apr. 10, 1979

[54] PHOTOGRAPHIC MATERIAL CONTAINING AN ORGANO-TELLURIUM COMPOUND A 1,4-DIHYDROPYRIDINE PHOTO-OXIDIZING AGENT AND THE USE THEREOF IN HEAT DEVELOPMENT

[75] Inventors: Julius L. Vuyts; Frans C. Heugebaert, both of Kontich; Wilhelmus Janssens, Aarschot, all of Belgium

[73] Assignee: AGFA-Gevaert N.V., Mortsel, Belgium

[21] Appl. No.: 882,044

[22] Filed: Feb. 28, 1978

[30] Foreign Application Priority Data

Mar. 2, 1977 [GB] United Kingdom ............... 8760/77

[51] Int. Cl.$^2$ .......................... G03C 5/24; G03C 1/00
[52] U.S. Cl. ..................................... 96/48 HD; 96/88
[58] Field of Search ................... 96/88, 48 HD, 114.1

[56] References Cited

U.S. PATENT DOCUMENTS

3,901,710  8/1975  Ranz et al. .................. 96/88
4,082,901  4/1978  Laridon et al. ............. 96/114.1

FOREIGN PATENT DOCUMENTS

2436132  2/1975  Fed. Rep. of Germany ........... 96/48

Primary Examiner—Won H. Louie, Jr.
Attorney, Agent, or Firm—William J. Daniel

[57] ABSTRACT

A photosensitive recording material containing in admixture in a binder medium:

(1) an imaging substance which is a tellurium tetrahalide or an organo-tellurium compound having a halogen atom directly linked to a tellurium atom and at least one organic substituent comprising a carbonyl group, (2) a photo-oxidizing agent which is a photosensitive 4-(2'-nitrophenyl)-1,4-dihydropyridine, and (3) a heat-activatable organic reducing agent or reducing agent precursor adapted to reduce the tellurium compound upon heating but leaving that compound substantially unaffected at and below 60° C.

14 Claims, 1 Drawing Figure

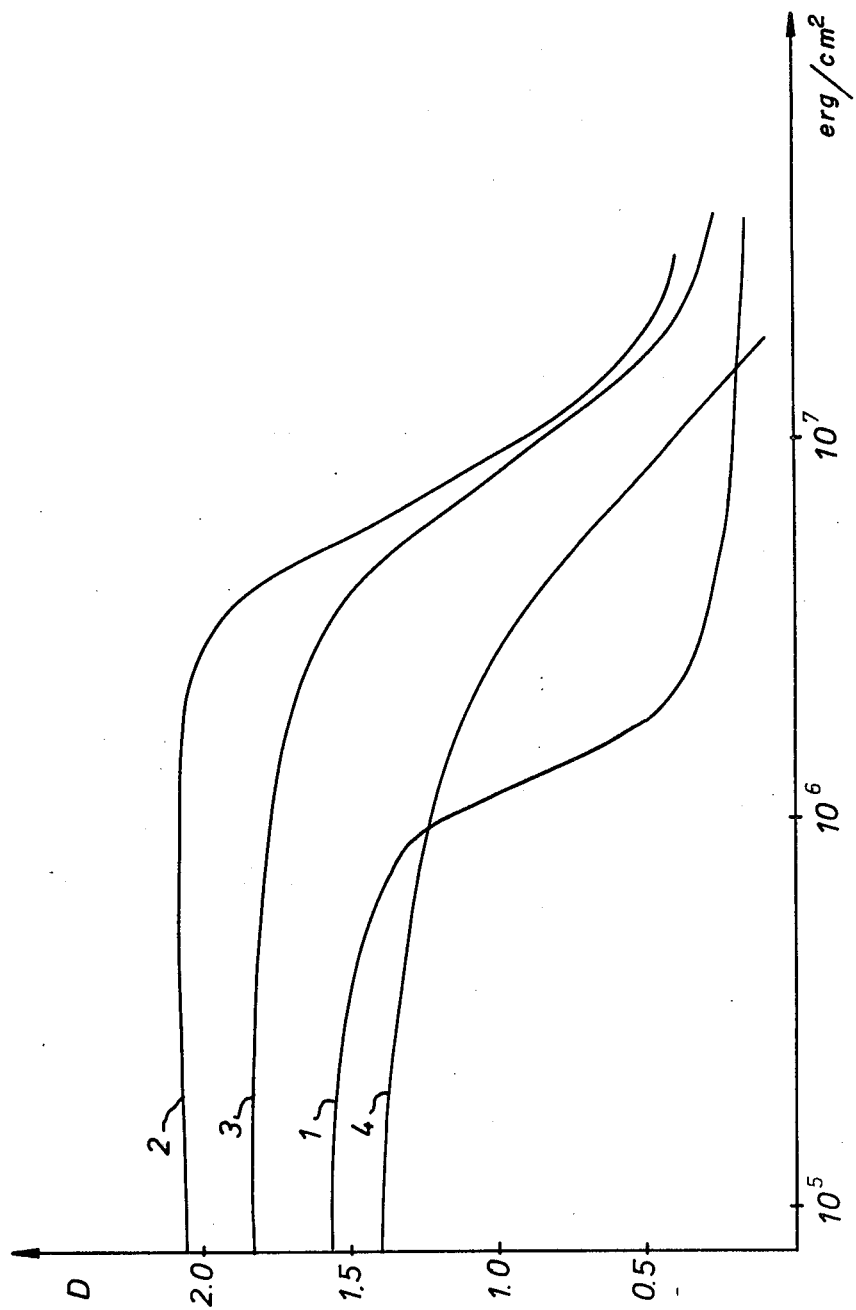

PHOTOGRAPHIC MATERIAL CONTAINING AN ORGANO-TELLURIUM COMPOUND, A 1,4-DIHYDROPYRIDINE PHOTO-OXIDIZING AGENT AND THE USE THEREOF IN HEAT DEVELOPMENT

The present invention relates to photosensitive recording materials and a method of recording information with such materials.

In the published German Patent Application (Dt-OS) No. 2,436,132 a method has been described for producing a record of retrievable information in which an organo-tellurium compound is used as imaging substance.

According to an embodiment of this process an imaging organo-tellurium compound containing halogen, preferably chlorine, linked directly to a tellurium atom and containing at least one organic substituent comprising a carbonyl group, is reduced image-wise with a photo-exposed photoreductant, e.g. a polynuclear quinone.

The following reaction scheme illustrates said process in which a tellurium image is formed:

PQ $\xrightarrow{h\nu}$ $^1$PQ → $^3$PQ $^3$PQ + 2RH → PQ.H$_2$ + R—R (R$^1$)$_2$.Te.Cl$_2$ + 2PQ.H$_2$ → 2PQ + 2R$^1$H + Te + 2HCl wherein:
PQ is photoreductant, e.g. phenanthrene quinone,
$^1$PQ is the first excited singlet of said quinone,
$^3$PQ is the triplet state of said quinone,
RH is a hydrogen donor, e.g. an organic hydroxy compound,
PQ.H$_2$ is the photoreductant in reduced state, and
(R$^1$)$_2$.Te.Cl$_2$ is a reducible organo-tellurium compound wherein R$^1$ is e.g., (C$_6$H$_5$COCH$_2$+.

With the imaging system described in this German Patent Application negative images of originals are produced.

The present invention provides a photosensitive recording material and process suitable for producing directly positive images through image-wise photo-exposure and overall heating.

In the photosensitive recording material according to the invention, a substance called "photo-oxidizing agent" is image-wise activated with actinic radiation to effect in the image areas thereof oxidation and de-activation or neutralization of a reducing compound that is capable of reducing at elevated temperature the already mentioned organo-tellurium compound. At room temperature (20° C.) such reducing compound is in an inactive state. It obtains the required reducing power to reduce the organo-tellurium compound by heating. Only in the areas that are non-photo-exposed or insufficiently exposed during the image-wise activation step is the reducing compound left unaffected by the photo-oxidant and thus in active condition for subsequent reduction at elevated temperature of the organo-tellurium compound to form a positive tellurium image.

The photosensitive recording material of the present invention contains in admixture in a binder medium:
(1) an imaging substance which is a tellurium tetrahalide, preferably tellurium tetrachloride, or an organo-tellurium compound containing halogen directly linked to a tellurium atom and at least one organic substituent comprising a carbonyl group,
(2) a photo-oxidizing agent which is a photosensitive 4-(2'-nitrophenyl)-1,4-dihydropyridine, and
(3) a heat-activatable organic reducing agent or reducing agent precursor adapted to reduce the tellurium compound upon heating but leaving that compound substantially unaffected at and below 60° C.

The reducing agent or reducing agent precursor is preferably one that passes the following assessment test.

Assessment Test

A 0.5% by weight solution of a selected compound as defined in (3) in an inert solvent, e.g. 1,1,2,2-tetrachloroethane, is mixed with a 0.5% by weight solution of bis(phenacyl) tellurium dichloride in the same solvent. A portion Y of the solution is heated in a test tube on a water-bath at 60° C. for 30 min. A portion Z equal to portion Y is heated on an oil-bath at 140° C. for 30 min. A perceptible precipitation of tellurium should not occur by during the treatment of portion Y, whereas by the treatment of portion Z a perceptible precipitate of tellurium has to be formed.

Reducing agent precursors that pass the above test are derived from pyrazolidin-3-one reductors, in which the active hydrogen atom in 2-position is temporarily blocked, e.g. by reaction with an organic isocyanate or an acid halide.

Other examples of reducing agents that are poor reductors with respect to the above type of tellurium compound at room temperature (20° C.) but become substantially more active above 60° C. are sulphonyl hydrazides corresponding to the following general formula:

R—SO$_2$—NH—NH$_2$ wherein:
R is an organic group, e.g. an alkyl or aryl group including such groups in substituted form.

Sulphonyl hydrazide compounds within the scope of the above formula are described as starting products for the preparation of sulphonyl-hydrazones in the U.S. Pat. No. 3,293,032.

Another class of reducing agents that are poor reductors with respect to said tellurium compound at room temperature (20° C.) but are effective above 60° C. are acylhydroxylamines representatives of which are described in the published German Patent Application (DT-OS) No. 2,415,603.

These compounds and suitable analogues are within the scope of one of the following general formulae (I), (II) or (III):

$$R^1-\underset{X}{\underset{\|}{C}}-NHOH \qquad (I)$$

$$R^1-CO-NH-NH-CH=NOH \qquad (II)$$

$$\begin{array}{c}R^2\\ \diagdown\\ N-SO_2-NHOH\\ \diagup\\ R^3\end{array} \qquad (III)$$

wherein:
R$^1$ represents (1) an aliphatic group e.g. an alkyl group, a cycloaliphatic group or an aryl group, e.g. a phenyl or naphthyl group including such groups in substituted form, (2) a —OR⁴ group wherein R⁴ is an alkyl or aryl group including such groups in substituted form, or (3) a $$-N\begin{matrix}R^5\\R^6\end{matrix}$$

group wherein each of $R^5$ and $R^6$, which may be the same or different, is hydrogen or represents an alkyl or an aryl group including such groups in substituted form or $R^5$ and $R^6$ together represent the atoms necessary to close a 5- or 6-membered heterocyclic ring e.g. a N-piperidine, N-morpholine or N-pyrrolidine ring, X represents O or NH, $R^2$ represents hydrogen, an alkyl or an aryl group including such groups in substituted form, $R^3$ represents an alkyl or aryl group including such groups in substituted form or $R^2$ and $R^3$ together represent the atoms to close a 5- or 6-membered heterocyclic ring e.g. a piperidine ring.

Representatives of these classes of compounds (3) for use according to the present invention are listed in the following Table 1.

Table 1

| Compound no. | Chemical structure | Melting point °C. |
|---|---|---|
| 1 | (structure) | 97 |
| 2 | (structure) | 182 |
| 3 | (structure) | 164 |
| 4 | H₃C—SO₂—NHNH₂ | 45 |
| 5 | H₃C—(CH₂)₁₁—SO₂—NHNH₂ | 75 |
| 6 | H₃C—(CH₂)₁₅—SO₂—NHNH₂ | 88 |
| 7 | (structure)—SO₂—NHNH₂ | 105 |
| 8 | (structure) | 120 |
| 9 | (structure) | 122 |
| 10 | (structure) | 145 |
| 11 | (structure) | 103 |
| 12 | (structure)—CONHNH—CH=NOH | 140 (decomp.) |
| 13 | H₃C—(CH₂)₄—CONHNH—CH=NOH | 130 (decomp.) |
| 14 | (structure) | oily at 20° C. |
| 15 | (structure) | oily at 20° C. |

Preparation of compound 1

1 Mole of chloroacetyl chloride was added to 1.2 mole of 1-phenyl-pyrazolidin-3-one and 1.2 mole of pyridine dissolved in 4 l of benzene.

After 2 h of refluxing the reaction mixture was cooled and washed with water. The benzene layer was separated and the benzene removed by evaporation. The residue was dissolved in ethyl acetate and hexane was added to precipitate compound 1. Melting point: 94° C.

Preparation of compound 2

1 Mole of 1-phenyl-pyrazolidin-3-one and 1 mole of benzoyl isocyanate in 1 l of toluene were refluxed. The reaction mixture was cooled and the resulting solid compound 2 was separated. Melting point: 182° C.

Preparation of compound 3

1 Mole of 1-phenyl-3,3'-dimethyl-pyrazolidin-3-one and 1 mole of benzoyl isocyanate in 1 l of toluene were refluxed. The reaction mixture was cooled and the resulting solid compound 3 was separated. Melting point: 163° C.

Preparation of compound 4

1 Mole of methylsulphonyl chloride was dissolved in 1 l of dioxan and added dropwise at room temperature to 1.2 mole of hydrazine hydrate dissolved likewise in dioxan. After filtration the dioxan was removed by evaporation. The residue was washed with ethanol. The washed product was separated by suction. Melting point: 45° C.

Preparation of compounds 5, 6 and 8

1 Mole of n-dodecylsulphonyl chloride was dissolved in 1 l of dioxan and at room temperature added dropwise to 1.2 mole of hydrazine hydrate, dissolved likewise in dioxan. The obtained solution was diluted with water, cooled and the formed precipitate separated by suction. Melting point of compound 5: 75° C. Compound 6 and 8 were prepared analogously by the use of n-hexadecyl-sulphonyl chloride and 2,4,6-trimethyl-phenylsulphonyl chloride respectively. Melting point of compound 6: 88° C. Melting point of compound 8: 120° C.

Preparation of compound 7

1 Mole of phenylsulphonyl chloride was dissolved in 1 l of ethanol and at 0° C. added dropwise to 1.2 mole of hydrazine hydrate dissolved likewise in ethanol. The formed precipitate was separated. Melting point: 105° C.

Preparation of compound 9

1 Mole of N-piperidine carbamoyl chloride was added dropwise at room temperature to a solution of 1 mole of hydroxylamine hydrochloride and 2 moles of triethylamine. The precipitate was separated by suction and the filtrate concentrated by evaporation. The residue left was crystallized from toluene. Melting point: 122° C.

Preparation of compound 10

See Ber. 19 (1886) 1488. Melting point: 145° C.

Preparation of compound 11

1 mole of potassium carbonate was allowed to react with 1 mole of hydroxylamine hydrochloride in 1 l of ether and 50 ml of water. After the expulsion of the produced carbon dioxide 1 mole of phenyl chloroformate was added dropwise. After the termination of the carbon dioxide production the formed potassium chloride was removed by filtering, the ether layer was separated and the ether was evaporated.

Melting point: 103° C.

Preparation of compounds 12 and 13

1 Mole of benzoylhydrazide, 1 mole of ethyl orthoformate, 1 mole of hydroxylamine hydrochloride and 1 mole of triethylamine were boiled at reflux temperature in methanol. The obtained reaction mass was concentrated by evaporation till dry. The obtained residue was washed with water.

Melting point of compound 12: 140° C. (decomposition).

Compound 13 with melting point 130° C. (decomposition) was prepared analogously but starting with caproyl hydrazide instead of with benzoyl hydrazide.

Preparation of compounds 14 and 15

1 Mole of N-piperidinesulphonyl chloride was added dropwise to a solution of 1 mole of hydroxylamine hydrochloride and 2 moles of triethylamine in methanol. The obtained solution was concentrated by evaporation. The residue was redissolved in methylene chloride and washed with a little water whereupon the methylene chloride layer was separated and the solvent was evaporated. Compound 14 was obtained as an oily product. Compound 15 was prepared analogously but starting with diethylaminosulphonyl chloride instead of with piperidylsulphonyl chloride. An oily product was obtained likewise.

4-(2′-nitrophenyl)-1,4-dihydropyridine derivatives that are particularly suited as photo-oxidizing agent for use according to the present invention are within the scope of the following general formula:

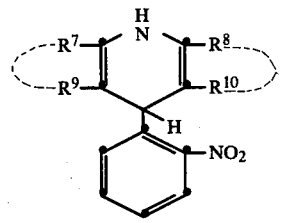

wherein:
each of $R^7$ and $R^8$ which may be the same or different, represents hydrogen or an alkyl group, preferably with up to 4 carbon atoms,
each of $R^9$ and $R^{10}$ which may be the same or different, represents cyano or an acyl group, preferably an acyl group derived from aliphatic carboxylic acids, particularly those with up to 5 carbon atoms, or the group $COOR^{11}$ in which $R^{11}$ represents an alkyl, alkenyl, alkynyl or cycloalkyl group preferably containing up to 6 carbon atoms, or an alkyl chain which may be interrupted by one or more hetero atoms such as oxygen or by imino groups; $R^7$ and $R^9$, and/or $R^8$ and $R^{10}$ may also represent together the ring members required for completing a 5- or 6-membered carbocyclic or heterocyclic ring, which may contain a carbonyl group as is present, e.g. in a cyclohexenone ring, and which may carry substituents, e.g. alkyl having preferably up to 4 carbon atoms such as methyl or ethyl.

The photo-oxidizing agents listed in the following table 2 have proved to be particularly suitable.

Table 2

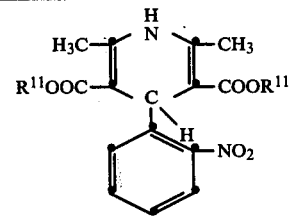

| Compound | $R^{11}$ | ° C. Melting point |
|---|---|---|
| A | —$CH_3$ | 172–173 |
| B | —$C_3H_7$ | 90 |
| C | —$CH_2$—C≡CH | 108 |
| D | —$CH_2$—$CH_2$—O—$C_2H_5$ | 93–96 |

These compounds and other compounds within the scope of the above general formula are prepared according to the U.S. Pat. No. 3,901,710.

Reducible organo-tellurium compounds that yield good results in the process of the present invention correspond to the following general formula:

$$R_xTeCl_y$$

wherein:
R represents an organic group, which is linked by a carbon atom to the tellurium atom and contains at least one carbonyl group,
x is 1, 2 or 3, and
x+y=4.

Such compounds as well as their preparation are described in the published German Patent Application (DT-OS) No. 2,436,132.

A preferred class of imaging agents are organo-tellurium compounds corresponding to the following general formula:

(Ar—CO—CH$_2$)$_2$TeCl$_2$ wherein:
Ar stands for an aromatic group including a substituted aromatic group, e.g. phenyl, methoxyphenyl, tolyl, or naphthyl. Bis(phenacyl)-tellurium dichloride is a preferred imaging agent for use according to the present invention.

The photosensitive recording materials according to the present invention contain the tellurium compound, photo-oxidizing agent and heat-activatable reducing agent or reducing agent precursor in admixture in a binder medium.

Particularly suitable binders for use in recording materials according to the present invention are organic polymeric substances including mixtures thereof.

Illustrative thereof are cyanoethylated starches, celluloses and amyloses having a degree of substitution of cyano-ethylation of at least 2; polyvinyl-benzophenone; polyvinylidene chloride; polyethylene terephthalate; cellulose esters and ethers such as cellulose acetate, cellulose propionate, cellulose butyrate, methylcellulose, ethylcellulose, hydroxypropylcellulose; polyvinylcarbazole; polyvinyl chloride; polyvinyl methyl ketone; polyvinyl alcohol; polyvinylpyrrolidine; polyvinyl methyl ether; polyacrylic and polymethacrylic alkyl esters such as polymethyl methacrylate and polyethyl methacrylate; copolymer of polyvinyl methyl ether and maleic anhydride; various grades of polyvinylformal resins such as so-called 12/85, 6/95 E, 15/95 S, 15/95 E, B-79, B-98, and the like, sold under the trademark "FORMVAR" — (Monsanto Chemical Company, St. Louis, Mo., USA). Particularly useful is polyvinylformal 15/95 E, which is a white, free-flowing powder having a molecular weight in the range of 24,000–40,000 and a formal content expressed as % polyvinylformal of approximately 82%, possessing high thermal stability, excellent mechanical durability, and resistance to such materials as aliphatic hydrocarbons and mineral, animal, and vegetable oils.

A dry photographic coating containing the above-mentioned ingredients can be formed by dissolving the binding agent or mixture of binding agents in a suitable inert solvent, which acts as a dispersing or dissolving medium for the other ingredients and which is removed from the coating composition by evaporation so that a solid photographic recording layer on a properly chosen support is left. The supports may be of any kind encountered in silver halide photographic materials, e.g. paper and resin film.

The coverage of the tellurium compound is preferably in the range of 1 to 10 g per sq.m.

The amount of heat-activatable reducing agent or reducing agent precursor is preferably at least equimolar with respect to the tellurium compound.

The amount of photo-oxidizing agent is preferably at least equimolar with respect to the heat-activatable reducing agent or reducing agent precursor, although smaller amounts can be used.

The present invention includes a recording method in which the above defined recording material is used. This method includes the steps of information-wise exposing this material to actinic radiation to which the photo-oxidizing agent is sensitive, preferably ultraviolet radiation, and overall heating above 60° C. to develop a tellurium image in the nonphotoexposed parts of the material.

The heat-development generally lasts approximately 30 s to 300 s depending on the temperature, which normally is in the range of from 80° to 200° C.

The heat required to produce the metal image can be supplied in various ways. So, the recording material can be developed by heat transport from hot bodies, e.g. plates or rollers, or by contact with a hot gas stream, e.g. hot air. Furthermore, the metal image can be formed by means of infrared radiation.

The following examples illustrate the present invention without, however, limiting it thereto.

All parts, percentages or ratios are by weight, unless otherwise indicated.

EXAMPLE 1

1.6 g of compound A of Table 2, 1.1 g of compound 1 of table 1 and 1.5 g of bis(phenacyl)-tellurium dichloride were dissolved in a mixture of 20 ml of methylene chloride and 20 ml of tetrahydrofuran.

The solution obtained was mixed with 40 g of a 20% solution of VINYLITE VAGH (trade name of Union Carbide and Carbon for a copoly(vinyl chloride/vinyl acetate/vinyl alcohol) (91/3/6)) in methyl ethyl ketone and 1 ml of 2% solution of silicone oil in methylene chloride as coating aid.

The coating composition obtained was applied by dip-coating to a polyethylene terephthalate film support at a coverage of 2 g of said organo-tellurium compound per sq.m.

The coating was dried with ventilation at 30° C. for 4 h and afterwards at 45° C. for 18 h.

Processing

The resulting photosensitive recording material was exposed for 100 s through a step wedge with a constant of 0.3 in the "SPEKTRAPROOF" (trade name of Siegfried Theimer GmbH, 6481 Obersatzbach, W. Germany) exposure apparatus equipped with a 2000 W lamp emitting with a maximum at about 350 nm.

The exposed material was developed by heating at 160° C. for 5 min. The obtained curve of density (D) versus photon-exposure energy per sq.cm. (erg/sq.cm) is presented in the FIGURE as curve 1.

EXAMPLE 2

1.6 g of compound A of Table 2, 1.05 g of compound 8 of Table 1, and 1.5 g of bis(phenacyl)-tellurium dichloride were dissolved in a mixture of 20 ml of methylene chloride and 20 ml of tetrahydrofuran. The solution obtained was mixed with 50 g of a 20% solution of VINYLITE VAGH (trade name) in methyl ethyl ketone and 1 ml of 2% silicone oil in methylene chloride as coating aid.

Coating, drying, and processing proceeded as in Example 1, whereas the development of the exposed material proceeded by heating at 160° C. for only 1 min.

The obtained density (D) versus erg/sq.cm curve is presented in the FIGURE as curve 2.

EXAMPLE 3

3.2 g of compound A of Table 2, 0.6 g of compound 9 of Table 1, and 0.75 g of tellurium tetrachloride were dissolved in a mixture of 20 ml of methylene chloride and 30 ml of methyl ethyl ketone. The solution obtained was mixed with 40 g of a 20% solution of VINYLITE VAGH (trade name) in methyl ethyl ketone and 1 ml of 2% silicone oil in methylene chloride as coating aid.

Coating, drying, and processing, proceeded as in Example 1, whereas the development of the exposed material proceeded by heating at 160° C. for 3 min.

The obtained density (D) versus erg/sq.cm curve is presented in the FIGURE as curve 3.

EXAMPLE 4

2.9 g of compound D of Table 2, 0.6 g of compound 9 of Table 1, and 1.5 g of bis(phenacyl)-tellurium dichloride were dissolved in a mixture of 10 ml of methyl ethyl ketone and 15 ml of tetrahydrofuran. The solution obtained was mixed with 40 g of a 20% solution of VINYLITE VAGH (trade name) in methyl ethyl ketone and 10 ml of a 0.2% of silicone oil in methylene chloride as coating aid.

Coating, drying, and processing proceeded as in Example 1, whereas the development of the exposed material proceeded at 140° C. for 3 min.

The obtained density (D) versus erg/sq.cm curve is presented in the FIGURE as curve 4.

We claim:

1. A photosensitive recording material containing in admixture in a binder medium:
   (1) an imaging substance which is a tellurium tetrahalide or an organo-tellurium compound having a halogen atom directly linked to a tellurium atom and at least one organic substituent comprising a carbonyl group,
   (2) a photo-oxidizing agent which is a photosensitive 4-(2'-nitrophenyl)-1,4-dihydropyridine, and
   (3) a heat-activatable organic reducing agent or reducing agent precursor that is adapted to reduce said tellurium compound by heating but leaves that compound substantially unaffected at and below 60° C.

2. A material according to claim 1, wherein said reducing agent or reducing agent precursor passes the assessement test herein defined on page 3 of the specification.

3. A material according to claim 1, wherein the tellurium compound is tellurium tetrachloride or an organo tellurium compound corresponding to the following general formula:

$$R_xTeCl_y$$

wherein:
R represents the organic group, which is linked by a carbon atom to the tellurium atom and contains at least one carbonyl group,
x is 1, 2, or 3, and
$x+y=4$.

4. A material according to claim 3, wherein the organo-tellurium compound corresponds to the following general formula:

$$(Ar-CO-CH_2)_2TeCl_2$$

wherein Ar stands for an aromatic group.

5. A material according to claim 4, wherein the organo-tellurium compound is bis(phenacyl)-tellurium dichloride.

6. A material according to claim 1, wherein the photo-oxidizing agent corresponds to the following general formula:

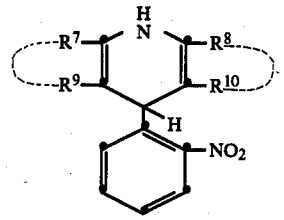

in which:
R[7] and R[8] represent hydrogen or an alkyl group and are the same or different,
and R[9] and R[10] represent cyano or an acyl group or a COOR[11] group, in which R[11] represents an alkyl, alkenyl, alkynyl or cycloalkyl group or an alkyl chain interrupted by one or more hetero atoms or by imino groups and are the same or different,
or R[7] and R[9] and/or R[8] and R[10] represent together the ring members required for completing a carbocyclic or heterocyclic ring which may contain a carbonyl group and may carry substituents.

7. A material according to claim 6, wherein each of R[7] and R[8] represents methyl, and each of R[9] and R[10] represents a —COOR[11] group, in which R[11] is methyl, butyl, —CH$_2$—C≡CH or —(CH$_2$)$_2$—O—C$_2$H$_5$.

8. A material according to claim 1, -one conductor, wherein the heat-activatable reducing agent precursor is a pyrazolidin-3-onereductor, in which the active hydrogen atom in 2-position is temporarily blocked by reaction with an organic isocyanate or with an acid halide.

9. A material according to claim 1, wherein the heat-activatable reducing agent is a sulphonylhydrazide compound corresponding to the following general formula:

$$R-SO_2-NH-NH_2$$

wherein R is an organic group.

10. A material according to claim 1, wherein the heat-activatable reducing agent is a compound corresponding to one of the following general formulae (I), (II) or (III):

$$R^1-\underset{\underset{X}{\|}}{C}-NHOH \qquad (I)$$

$$R^1-CO-NH-NH-CH=NOH \qquad (II)$$

$$\underset{R^3}{\overset{R^2}{\diagdown}}N-SO_2-NHOH \qquad (III)$$

wherein:
R[1] represents
(1) an aliphatic group, a cycloaliphatic group or an aryl group,
(2) a —OR[4] group wherein R[4] is an alkyl or aryl group, or
(3) a

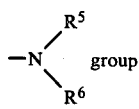

group wherein $R^5$ and $R^6$ represent hydrogen, an alkyl or an aryl group and are the same or different, or $R^5$ and $R^6$ together represent the atoms necessary to close a 5- or 6-membered heterocyclic ring, X represents O or NH, $R^2$ represents hydrogen, an alkyl or an aryl group, and $R^3$ represents an alkyl or an aryl group, or $R^2$ and $R^3$ represent together the necessary atoms to close a 5- or 6-membered heterocyclic ring.

11. A material according to claim 1, wherein the binder medium is composed of a polymeric organic substance.

12. A material according to claim 1, wherein the photo-oxidizing agent is present in at least equimolar amounts with respect to the heat-activatable reducing agent or reducing agent precursor.

13. A recording process, wherein a photosensitive recording material containing in admixture in a binder medium:

(1) an imaging substance which is a tellurium tetrahalide or an organo-tellurium compound wherein halogen is directly linked to a tellurium atom and at least one organic substituent comprises a carbonyl group, (2) a photo-oxidizing agent which is a photosensitive 4-(2'-nitrophenyl)-1,4-dihydropyridine, and (3) a heat-activatable organic reducing agent or reducing agent precursor that can be caused to reduce said tellurium compound by heating but leaves that compound substantially unaffected at and below 60° C., is information-wise exposed to actinic radiation to which the photo-oxidizing agent is sensitive and the exposed material is overall heated above 60° C. to develop a tellurium image in the non-photo-exposed areas.

14. A recording process according to claim 13, wherein the heating proceeds in the temperature range of 80° to 200° C.

* * * * *